United States Patent [19]
Sekiya

[11] Patent Number: 5,623,553
[45] Date of Patent: Apr. 22, 1997

[54] HIGH CONTRAST FINGERPRINT IMAGE DETECTOR

[75] Inventor: Takaomi Sekiya, Tokyo, Japan

[73] Assignee: Asahi Kogaku Kogyo Kabushiki Kaisha, Tokyo, Japan

[21] Appl. No.: 525,069

[22] Filed: Sep. 8, 1995

Related U.S. Application Data

[63] Continuation of Ser. No. 259,977, Jun. 17, 1994, abandoned.

[30] Foreign Application Priority Data

Jun. 21, 1993 [JP] Japan .................................. 5-148774

[51] Int. Cl.⁶ ..................................................... G06K 9/00
[52] U.S. Cl. ................................................. 382/127; 356/71
[58] Field of Search ........................... 340/825.3, 825.34; 356/71; 382/124, 127, 321

[56] References Cited

U.S. PATENT DOCUMENTS

| | | | |
|---|---|---|---|
| 3,292,149 | 12/1966 | Bourne | 340/146.3 |
| 4,783,167 | 11/1988 | Schiller et al. | 356/71 |
| 4,924,085 | 5/1990 | Kato et al. | 250/227.28 |
| 5,109,427 | 4/1992 | Yang | 382/4 |
| 5,177,802 | 1/1993 | Fujimoto et al. | 382/4 |
| 5,233,404 | 8/1993 | Lougheed et al. | 356/71 |
| 5,416,573 | 5/1995 | Sartor, Jr. | 356/71 |

FOREIGN PATENT DOCUMENTS

| | | | |
|---|---|---|---|
| 0045913 | 2/1982 | European Pat. Off. | 356/71 |
| 55-13446 | 1/1980 | Japan | G06K 9/20 |
| 58-144280 | 8/1983 | Japan | G06K 9/00 |
| 2-270087 | 11/1990 | Japan | 382/4 |
| 3-194677 | 8/1991 | Japan | 382/4 |
| 89/03099 | 4/1989 | WIPO | 382/4 |

OTHER PUBLICATIONS

English Translation of European Patent Application 045 913 to Rüll et al., publ. Feb. 1982.
English Translation of Japanese Kokai 3-194677 to Takeda et al., publ. Aug. 1991.
English Translation of Japanese Kokai 2-270087 to Shindo, publ. Nov. 1990.

Primary Examiner—Andrew Johns
Attorney, Agent, or Firm—Greenblum & Bernstein P.L.C.

[57] ABSTRACT

In a fingerprint input apparatus used to detect an image of a fingerprint, light is emitted towards a finger which is placed on an image detecting surface of a prism. An incident angle of light on the image detecting surface is less than a critical angle. An image sensor detects light which has been diffused by the fingerprint and directed towards the image sensor.

15 Claims, 10 Drawing Sheets

HIGH CONTRAST FINGERPRINT IMAGE DETECTOR

This application is a continuation of application No. 08/259,977, filed Jun. 17, 1994, now abandoned.

BACKGROUND OF THE INVENTION

The present invention relates to a fingerprint input apparatus, for example, used in a system that verifies an identity of an individual in a security system.

Conventional fingerprint input apparatuses which detect fingerprints as an optical image are disclosed in Japanese Patent Publication SHO 55-13446 and Japanese Patent Publication SHO 58-144280.

In one conventional fingerprint input apparatus, a finger is placed on a plane surface of an optically transparent material. A light source is positioned such that the light emitted therefrom is incident on the plane surface at an angle greater than the critical angle. Some of the incident light will be scattered while that corresponding to the fingerprint will be reflected. An image sensor is positioned to receive the reflected light, thereby detecting the fingerprint pattern. However, the positioning of the image sensor must be done carefully if the reflected light is to be received properly. Further, interference from the scattered light reduces the contrast of the light received at the image sensor, and reduces the quality of the fingerprint pattern detected.

In another conventional fingerprint input apparatus, a similar construction to that described above is employed. However, the image sensor is positioned so as not to receive any of the light reflected by the fingerprint. Thus, only the scattered light is detected, and the fingerprint pattern is detected as a result of an absence of light. However, the amount of light incident on the image sensor is low, and therefore the contrast is also low. Further, the positioning of the image sensor and the light source must be done carefully if direct interference from the light source on the image sensor is to be avoided.

SUMMARY OF THE INVENTION

It is therefore an object of the present invention to provide a fingerprint input apparatus which can detect a high contrast image of a fingerprint, thereby improving the accuracy of the image detected.

For accomplishing the object, according to invention, there is provided a fingerprint input apparatus used to detect an image of a fingerprint which includes:

an optical transparent block having an index of refraction which is greater than an index of refraction of a medium surrounding the optical transparent block; the optical transparent block has an image detecting surface where a finger is placed on at least a portion of the image detecting surface.

The fingerprint input apparatus also includes a light emitting device for emitting light towards the image detecting surface where the light emitting device is positioned such that the emitted light is incident on the image detecting surface at an angle less than a critical angle from within the optical transparent block.

The fingerprint input apparatus further includes an image sensing mechanism for receiving only the light diffused at the image detecting surface and directed to the image sensing mechanism.

DESCRIPTION OF THE EMBODIMENTS

Figure 1:
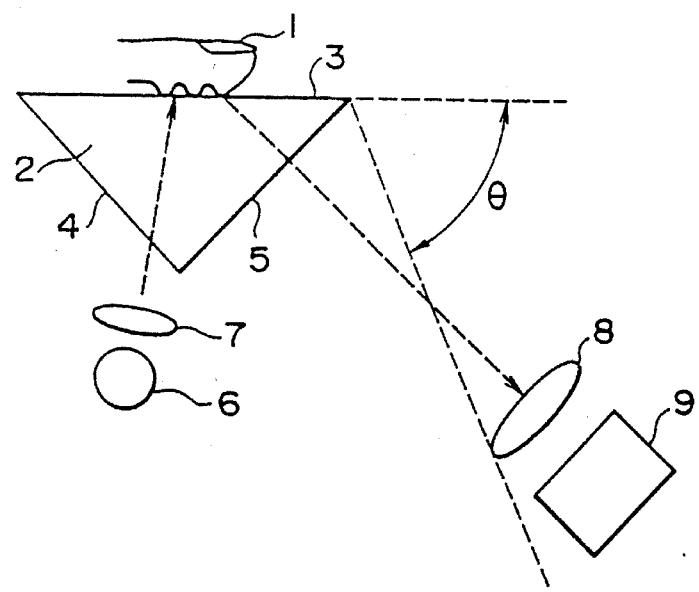
FIG. 1 shows a schematic drawing of a prism, a light source and a detector according to a first embodiment of the present invention.

FIG. 1 shows a first embodiment of a fingerprint input apparatus according to the present invention. A finger tip 1 is placed on a image detecting surface 3 of a prism 2. A light source 6 emits light which is projected by a lens group 7 to be incident on a plane surface 4 of the prism 2. The light is refracted and then incident on the image detecting surface 3 of the prism 2. The light source 6 and lens group 7 are arranged so that the light is incident on the image detecting surface 3 at an angle smaller than the critical angle of the image detecting surface 3.

Some of the light is diffused at the image detecting surface. The diffused light is incident on the plane surface 5, and then refracted. Some of the diffused light is then incident on a lens group 8 and then incident on an image sensor 9. The light that is incident on the image sensor 9 forms a pattern which can be image processed to form a pattern of a fingerprint of the finger tip 1.

The light source 6 can be a fluorescent tube, incandescent light bulb, light-emitting diode, an electro-luminescent source, or laser device. The image sensor 9 can be photographic film, a CCD sensor, or other sensors.

FIGS. 2 through 12 illustrate the theory behind the present invention.

Figure 2:
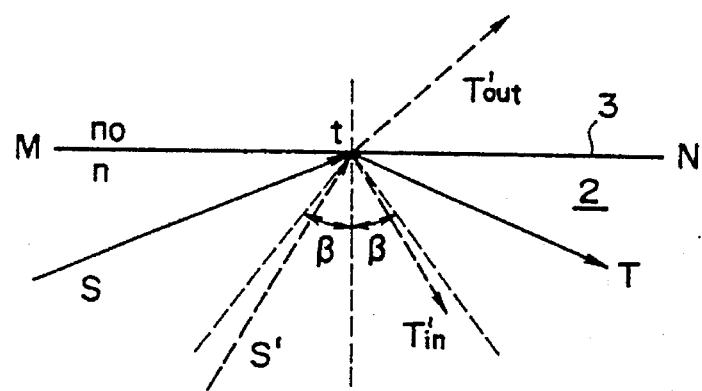
FIG. 2 is a ray diagram showing a light showing a light path of light transmitted from a prism to air.

In FIG. 2, plane MN represents the image detecting surface 3 shown in FIG. 1. In the embodiment shown in FIG. 1 the prism 2 is an optically transparent medium such as glass or acrylic which has a refractive index n. In FIG. 2 the medium having refractive index $n_0$ is air, where $n_0=1$. In this embodiment $n>0_)$. The critical angle of incidence $\beta$, measured from the normal line at the point of incidence of the light on the plane MN, is given by equation (1) below:

$$\beta = \sin^{-1}(1/n) \tag{1}$$

The light ray S has an angle of incidence which is larger than the critical angle $\beta$ and is totally internally reflected, shown by light ray T, at angle equal to the angle of incidence. The light ray S' has an angle of incidence which is smaller than the critical angle $\beta$ and thus some of the light is transmitted (i.e., refracted rays $T'_{out}$) while the remaining light is reflected (i.e., $T'_{in}$).

Figure 3:
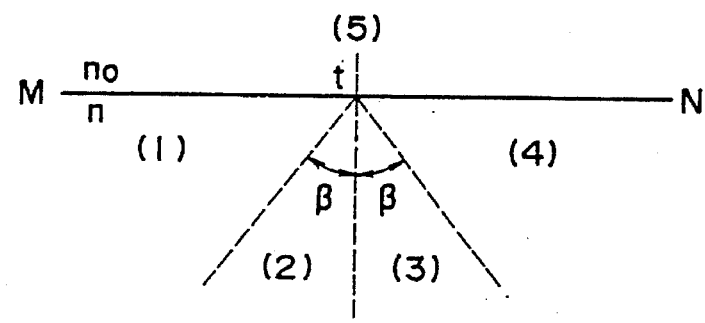
FIG. 3 is a ray diagram showing the conditions to achieve total internal reflection for the light path shown in FIG. 2.

As shown in FIG. 3, the light rays which are totally internally reflected are transmitted through regions (1) and (4) whereas the light rays which are refracted are transmitted through regions (2), (3) and (5).

Figure 4:
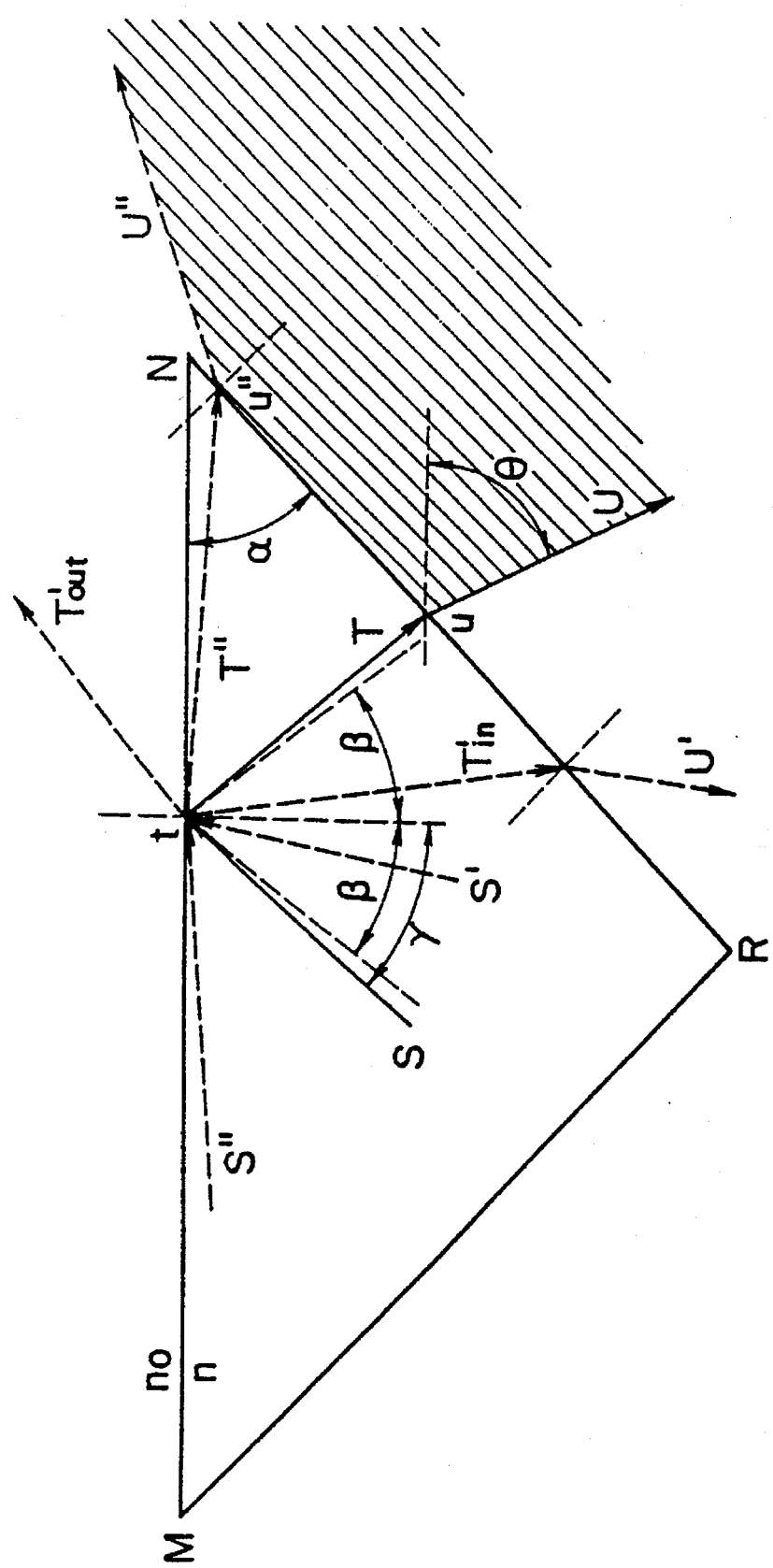
FIG. 4 shows paths taken by the light that is incident on an air-prism boundary surface for different angles of incidence.

If prism 2 is triangular, as shown in FIG. 4, the light rays S and S'' incident at the point t at greater angles than the critical angle $\beta$ are totally internally reflected as rays T and T'', respectively. Further rays, T and T'' exit the prism as refracted rays U and U'', respectively. The ray S' incident at the point t at a smaller angle than the critical angle $\beta$, has some light reflected (light ray t'in) and some light refracted (T'out). The reflected light T'in is then refracted, and exits the prism 2 as ray U'.

IN FIG. 4, the emerging angle $\theta$, measured clockwise with respect to a line parallel to plane MN, is given by equation (2) below:

$$\theta = (\pi/2) - \alpha + \sin^{-1}\{n \sin(\alpha-\gamma)\} \tag{2}$$

where $\gamma$ is the angle of incidence of the ray S, at the point t, measured from the normal line and $\alpha$ is the apical angle of point N.

In equation (2), if $\gamma=\beta$, then $\theta$ is defined as $\theta a$. Therefore, light incident at an angle less than the critical angle $\beta$, will exit at an angle greater than $\theta a$, conversely, light incident at an angle greater than the critical angle $\beta$, will exit at an angle less than $\theta a$.

Figure 5:
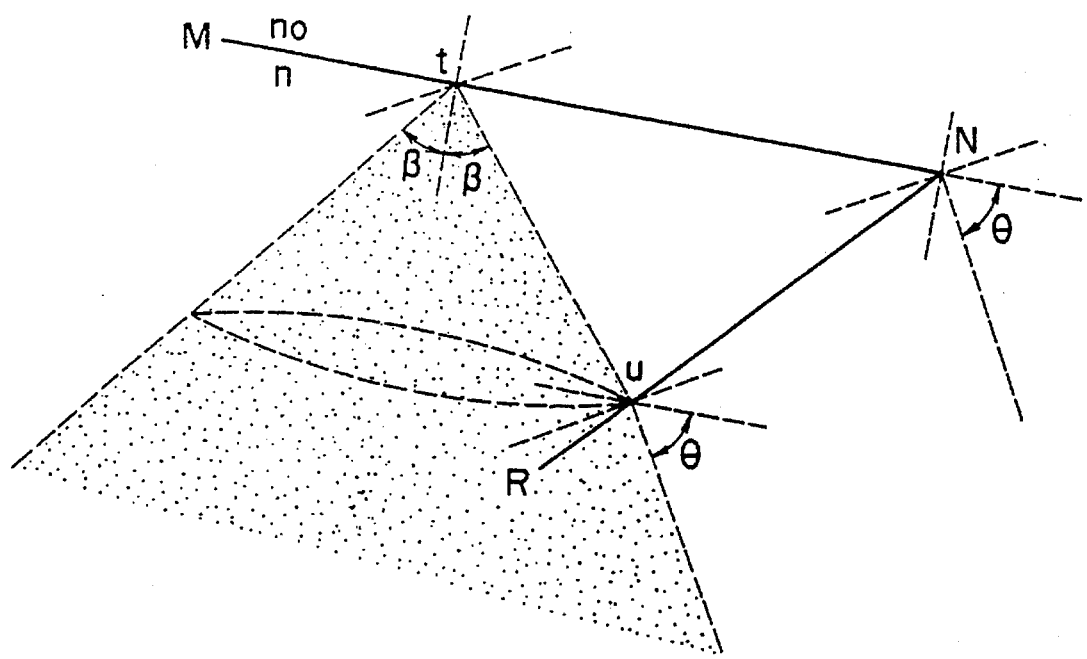
FIG. 5 shows a three dimensional view of the angles of incidence that a light path can have in order to avoid total internal reflection.

FIG. 5 shows a three dimensional view of the light paths shown in FIG. 4. The incident light must be emitted from within the cone (shown dotted) having an apical angle $2\beta$, in order not to be totally internally reflected.

Figure 6:
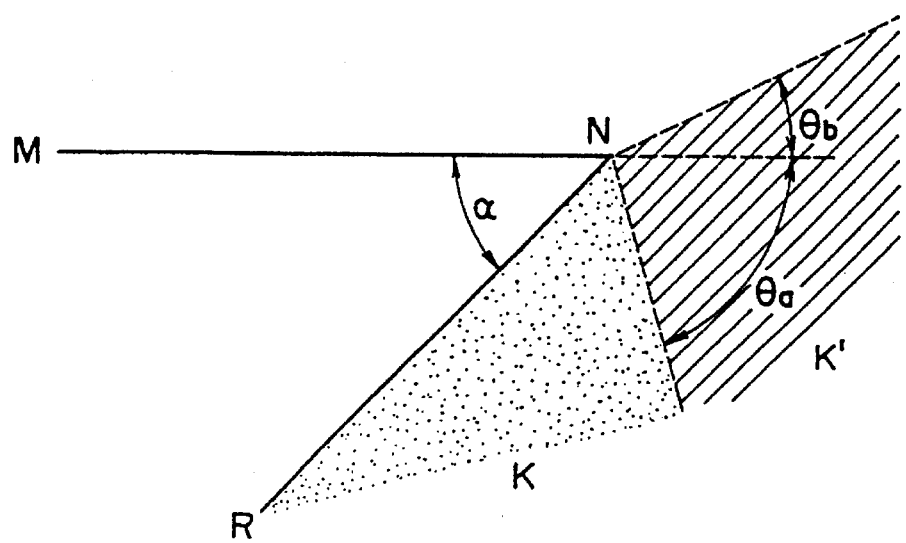
FIG. 6 shows the light path when light is incident at an end point N of the boundary surface MN of the prism.

FIG. 6 shows the case in which the point t is located infinitesimally close to the point N. In this case, the totally internally reflected light rays travel within the hatched region K', while the rays not totally internally reflected travel in the dotted region K. The angle $\theta$ can be either positive or negative depending on the incident angle. In FIG. 6, the maximum positive angle $\theta a$ is defined as the value of $\theta$ when the incident angle $\gamma$ approaches the limit of the critical angle $\beta$. Similarly, the maximum negative angle $\theta b$ is defined as the value of $\theta$ when incident angle $\gamma$ approaches the limit of $\pi/2$.

The fingerprint input apparatus according to the first embodiment of the present invention does not utilize the portion of the incident light rays which are totally internally reflected by the image detecting surface 3. Therefore, the light should be incident on the image detecting surface 3 at an angle less than the critical angle $\beta$. As a result, the prism 2 does not need to be triangular, as shown in FIGS. 4 and 6, but can other shapes.

Figure 7:
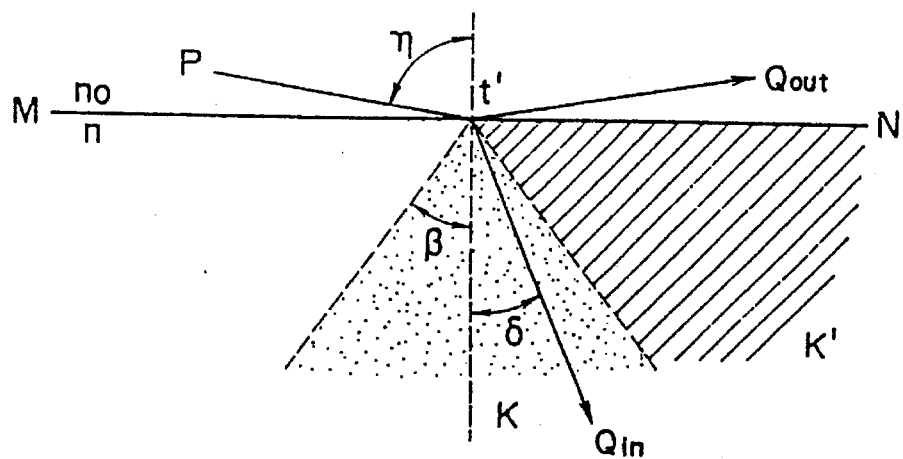
FIG. 7 shows a ray diagram of a light path of light incident on boundary surface MN when the light travels from the air to the prism.

FIG. 7 shows the light path of light incident on the boundary surface MN when the light travels from the air to the prism 2. The light ray P, which has an angle of incidence $\eta$ at point t', is divided into the ray $Q_{out}$ which is reflected at by the boundary surface MN and the refracted ray $Q_{in}$ that travels into the prism 2 at an refracted angle $\delta$. If the angle of incidence $\eta$ varies from 0 (zero) to $\pi/2$, then the refractive angle $\delta$ changes from 0 (zero) to $\beta$ accordingly.

Therefore, the ray $Q_{in}$ is limited to the dotted region K and does not enter the hatched region K'.

Figure 8:
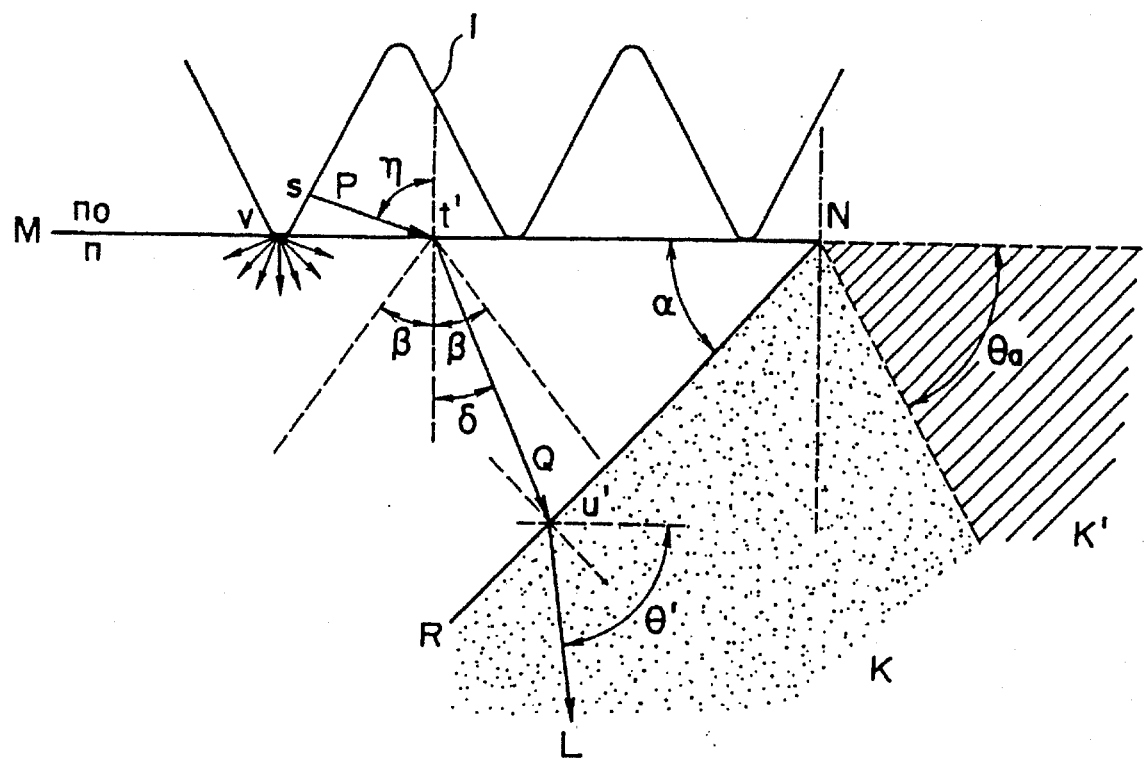
FIG. 8 shows a ray diagram of the light path when a finger is placed on the prism.

FIG. 8 shows the finger tip 1 placed on the boundary surface MN. The finger tip 1 is shown with an exaggerated scale. The portions of the finger tip 1 that do not contact the boundary surface MN represent the lines which make up a fingerprint, while the portion of the finger tip 1 that contacts the boundary surface MN represents the portion of the finger tip 1 which is between the lines of the fingerprint.

Light is incident on the boundary surface MN not in contact with the finger tip 1, i.e., directly below a line of the fingerprint, is refracted and then becomes incident on the surface of the finger tip 1 (e.g. point s in FIG. 8). A portion of the light is then reflected at the finger tip 1 back to the boundary MN (shown by ray P in FIG. 8) and becomes incident at point t' at angle $\eta$. The light is then refracted into the prism at angle $\delta$ (shown by ray Q) and then becomes incident at point u' of boundary surface RN. The ray is then refracted at emerging angle $\theta'$ (shown by ray L). The angle $\theta'$ is given by equation (3) below:

$$\theta' = (\pi/2) - \alpha + \sin^{-1}\{n \sin(\alpha-\delta)\} \tag{3}$$

The range of the angle $\delta$ is $0 \leq \delta \leq \beta$, and if $\delta=\beta$, then the minimum value of angle $\theta'$ is set $\theta'a$. Therefore, equation (2) and (3) are the same, resulting in $\theta a=\theta'a$. This shows that the light rays reflected by the lines of the fingerprints, the peripheral areas of the finger tip 1 or from the background, do not reach the hatched region K' shown in FIG. 8.

On the other hand, light that is incident on the boundary surface MN in contact with the finger tip 1, e.g. point v, is diffused in all directions.

Therefore, some of the light reflected from the boundary surface MN will emerge in the hatched region K', while the other light will emerge in the dotted region k. If the image sensor 9 is placed in the hatched region K', it will receive light reflected from the boundary surface MN which contacts the finger tip 1, but none of the light reflected from the boundary surface MN which does not contact the finger tip 1. Thus, the image obtained will be a high contrast representation of the fingerprint pattern.

FIG. 8 shows boundary surface MN being used to enable imaging of the fingerprint. However, in practice, the area near the ends of the surface (i.e., points M and N) are not used, and thus the dotted region K becomes smaller and the hatched region K' becomes larger.

Figure 9:
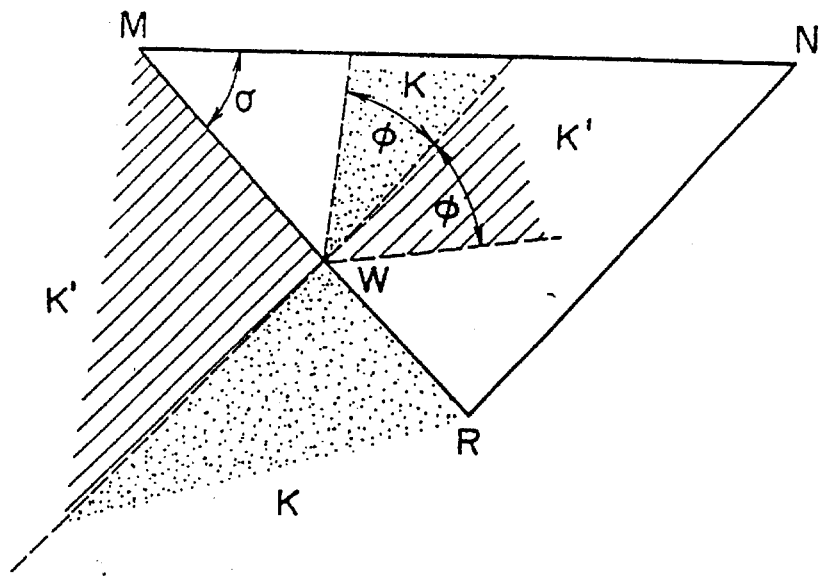
FIG. 9 is a diagram showing a region where light can be incident on a plane MR of the prism.

FIG. 9 shows the light rays incident on boundary surface MR of the prism. The light rays which are incident on point w and which are passed through the hatched region K' are refracted into the hatched region k' of the prism. Similarly, the light rays which are incident at point w on the boundary surface MR and which are passed through the dotted region K are refracted into the dotted region k of the prism. These regions are the areas delimited by the angles φ on both sides of the normal line at point w. The angle φ is the critical angle given by equation (4), which is similar to equation (1), and shown below:

$$\phi = \sin^{-1}(1/n) \qquad (4)$$

Since the refractive index n is the same as that in equation (1), the critical angle of incidence β equals the angle φ.

Figure 10:
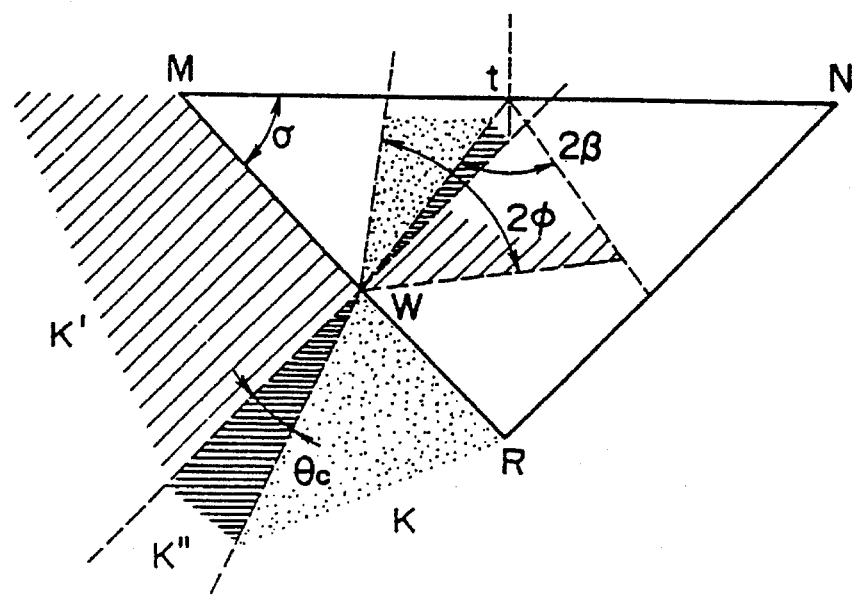
FIG. 10 shows a relationship between the light incident on plane MR and the critical angle of incidence on boundary surface MN.

In FIG. 10, the light rays which are transmitted through the hatched region K' above the normal line and are incident at the point w on the boundary surface MR, are refracted into the prism and are incident on the boundary surface MN at an angle greater than the critical angle β', and therefore, are totally internally reflected.

The light rays which enter the prism through the dotted region K below the normal line and are incident at point w on the boundary surface MR, are refracted into the prism and are incident on the boundary surface MN at an angle smaller than the critical angle β, and therefore, are not totally internally reflected. The light rays, which enter the prism through the region K" are refracted and are incident on the boundary surface MN at an angle greater than the critical angle β and therefore are totally internally reflected.

The angle θc between the normal line and the boundary line between the region K" and the dotted region K is given by equation (5) below:

$$\theta c = \sin^{-1}[(1/n) \sin \{\sigma + \beta - (\pi/2)\}] \qquad (5)$$

where σ is the angle between the boundary surface MN and the boundary surface MR. As described above, the light rays must enter the prism from below the normal line, and at the same time, at an greater angle than the angle θc in order to not to be totally internally reflected at the boundary surface MN.

Therefore, for the fingerprint input apparatus shown in FIG. 1, the light source 6 and projecting lens 7 should be positioned so that the light is incident below the normal line at an angle greater than the angle θc.

Thus, the light which is incident on the image detecting surface 3 (which corresponds to the boundary surface MN) that does not contact the finger tip 1, is reflected at an angle less than the critical angle and emerges with an angle greater than θa. The light which is incident on the image detecting surface 3 that is in contact with the finger tip 1, is reflected in all directions, with some of the light emerging at angle which is less than the angle θa. Further, to receive high contrast fingerprint images, the lens group 8 and image sensor 9 should be located in the area where only the light emerging at angle less than θa, will be incident.

In the above descriptions, a single light ray has been used to illustrate the path taken by the light. However, in the actual embodiments, a converging lens is used to converge a flux of light. Thus, the boundary rays of the light flux must be considered when determining the location of the light source 6 and image sensor 9.

Figure 11:
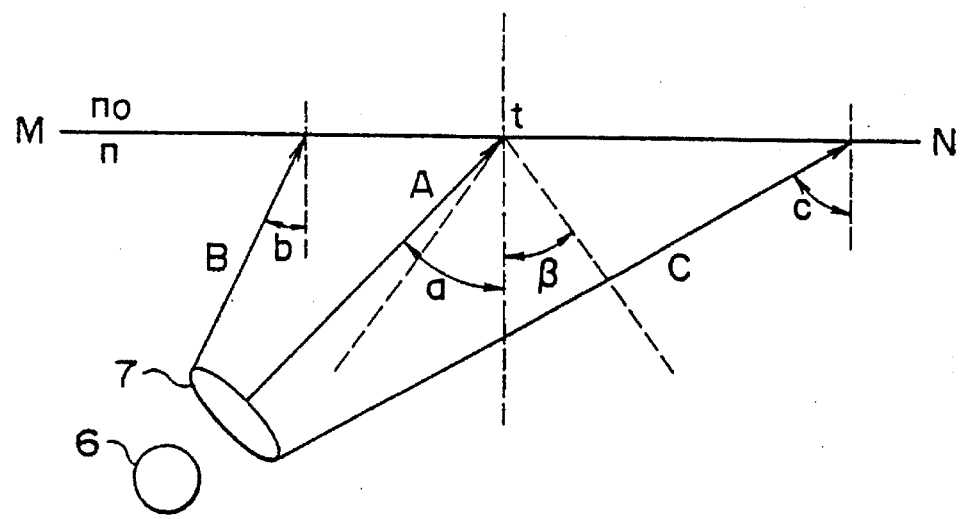
FIG. 11 is a ray diagram showing peripheral rays and a central ray of a beam of light which are incident on the boundary surface MN.

For example, as shown in FIG. 11, the main ray A, the peripheral ray B, and the peripheral ray C, which are emitted by the light source 6 and projected by the projection lens groups 7, are incident on the image detecting surface 3 at three points. The angles of incidence of each ray with respect to the critical angle β are a >β, b<β, and c>β. The main ray A and peripheral ray C are totally internally reflected while the peripheral ray B is not.

Figure 12:
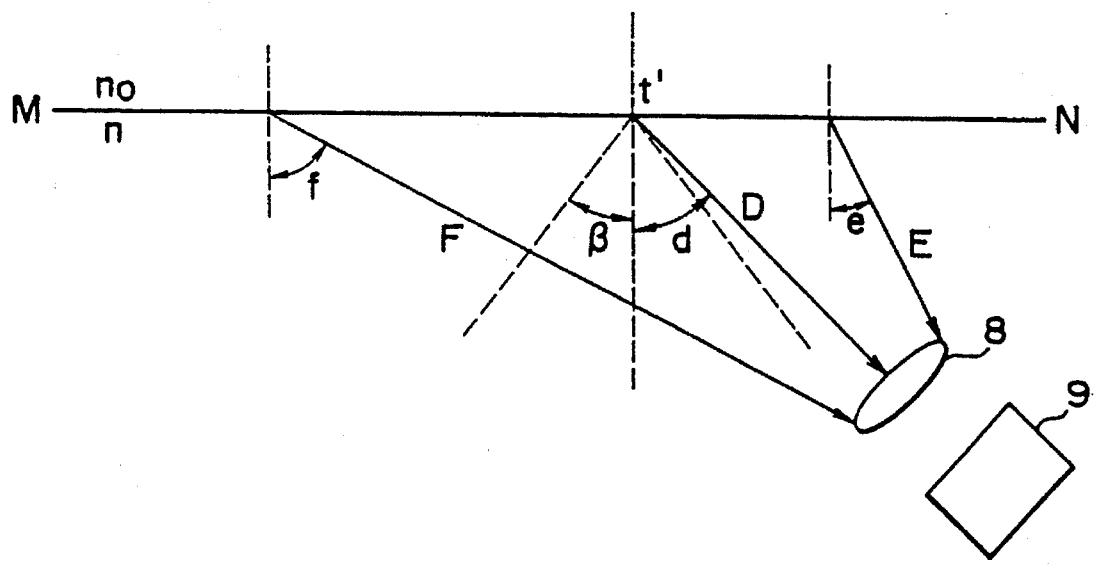
FIG. 12 shows the beam of light of FIG. 11 reflected toward an image sensor.

Similarly, as shown in FIG. 12, the main ray D, the peripheral ray E and the peripheral ray F are reflected towards the image sensor 9 at angles, measured from the normal line, of d, e and f respectively. The angles of reflection of each ray with respect to the critical angle β are d>β, e<β, and f>62. The ray E is reflected from a fingerprint line and may produce noise when it is incident on the image sensor 9, as shown in FIG. 12.

According to the description above, since a light flux is used, this must be considered when determining the positions of the light source 6 and the image sensor 9.

Figure 13:
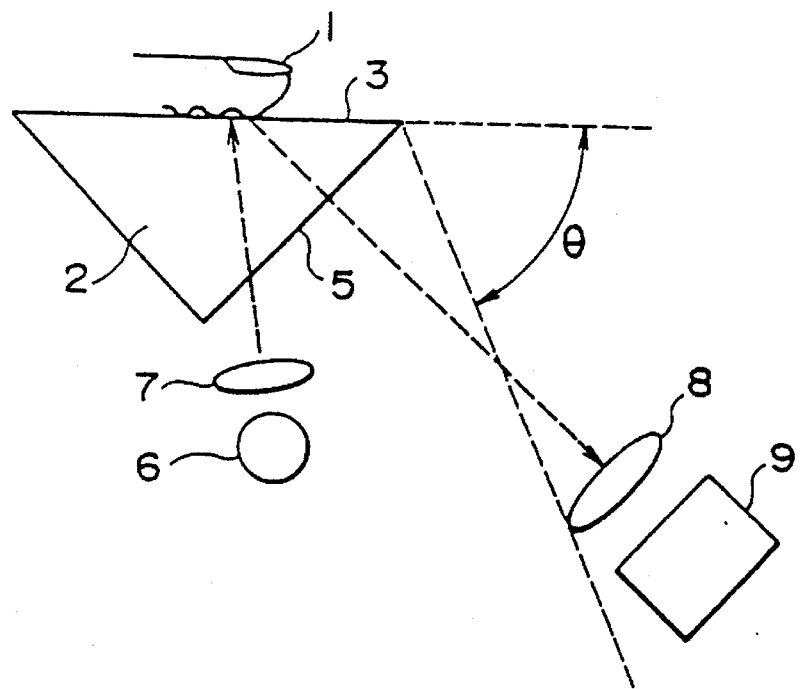
FIG. 13 shows a schematic drawing of a prism, light source and detector according to a second embodiment of the present invention.

FIG. 13 shows a second embodiment of the fingerprint input apparatus according to the present invention. A prism 2 similar to that used in the first embodiment is employed. However, in this embodiment, the incident light rays and the emerging light rays enter and leave the prism 2 through the same plane surface 5. In this embodiment, the light source 6 and projecting lens 7 are positioned so that the light is incident on the image detecting surface 3 at an angle which is less than the critical angle. Further, the lens group 8 and the image sensor 9 are positioned so that only the light which emerges at an angle less than the angle θ will be incident on the image sensor 9. In other words, only the light reflected from points on the image detecting surface 3 that contact the finger tip 1 will be incident on the image sensor 9. This results in a high contrast fingerprint image being detected by the image sensor 9.

Figure 14:
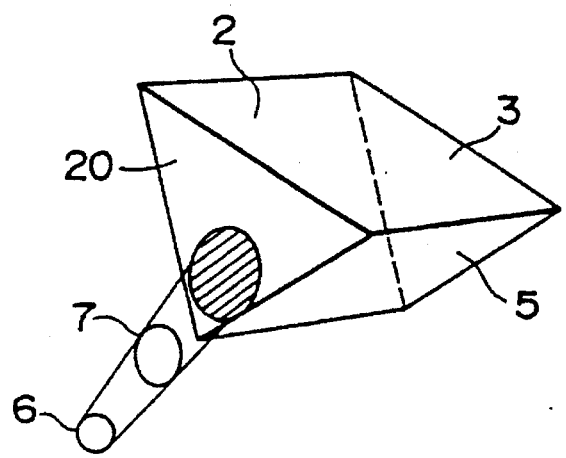
FIG. 14 shows a three dimensional view of the prism of FIG. 1 illuminated through a plane perpendicular to the plane of illumination shown in FIG. 1.

The light from the light source 6 may also be transmitted through the plane surface 20 as shown in FIG. 14, provided the above mentioned conditions are satisfied.

Figure 15:
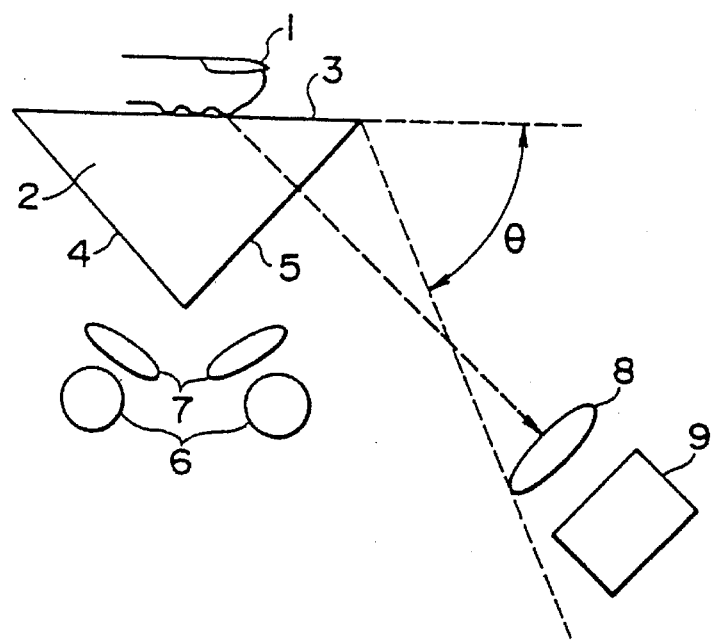
FIG. 15 shows a schematic drawing of a prism, light source and detector according to a third embodiment of the present invention.

In the third embodiment shown in FIG. 15, two light sources 6 and the lens groups 7 are employed to improve the uniformity of the illumination of the image detecting surface 3.

Figure 16:
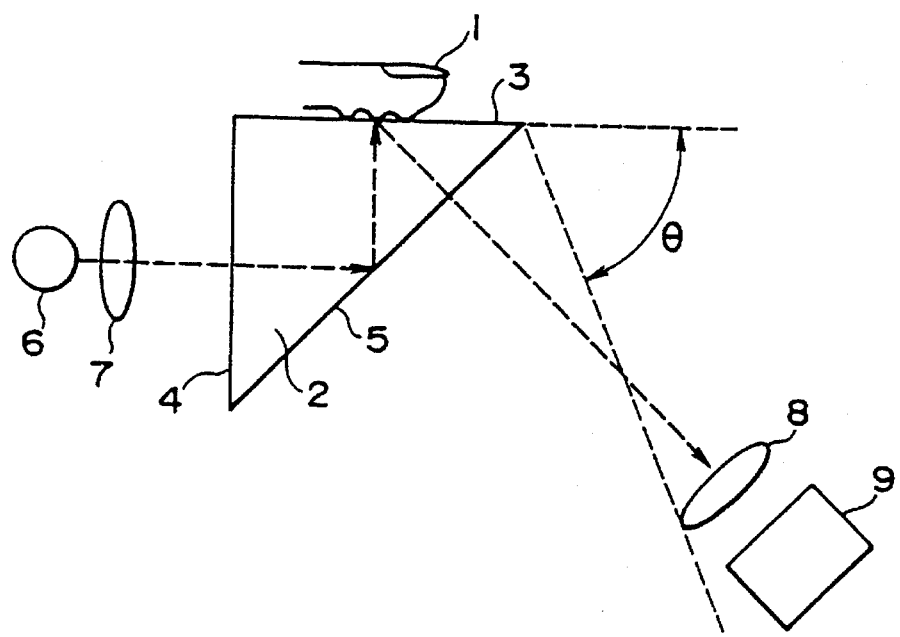
FIG. 16 shows a schematic drawing of a prism, light source and detector according to a fourth embodiment of the present invention.

FIG. 16 shows a fourth embodiment of the fingerprint input apparatus according to the present invention. In this embodiment, prism 2 is a right-angled prism. As shown in FIG. 16, the prism 2, light source 6, lens group 7, lens group 8 and image senor 9, are arranged such that the light emitted by the light source 6 is incident on the plane surface 4 at angle of 0° (i.e., perpendicular to the plane surface 4) and then incident on plane surface 5. The light is reflected at plane surface 5 and is incident on image detecting surface 3 at an incident angle of 0°. Thus, the image detecting surface is illuminated with light that is incident at an angle less than the critical angle.

Therefore, light which is incident on the image detecting surface 3 that is contact with the finger tip 1, will be reflected in all directions, whereas light, which is incident on the image detecting surface 3 directly below a line of the fingerprint, will be reflected such that it emerges at angle greater than θ. Therefore, the lens group 8 and image sensor 9 are placed in the region where light emerges from plane surface 5 at an angle less than θ, as shown in FIG. 16. In this way, no light corresponding to the lines of the fingerprint is received at the image sensor 9. However, light corresponding to the portion of the fingerprint between the lines is received at the image sensor 9, and thus, a high contrast image of the pattern of the fingerprint can be obtained.

Figure 17:
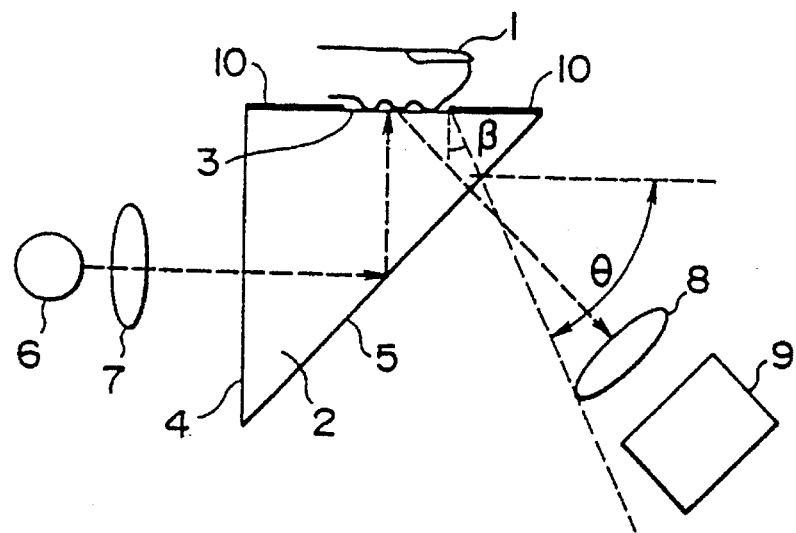
FIG. 17 shows a schematic drawing of a prism, light source and detector according to a fifth embodiment of the present invention.

FIG. 17 shows a fifth embodiment according to the present invention. The fingerprint input apparatus according the fifth embodiment is similar to the fourth embodiment shown in FIG. 16. The fifth embodiment further comprises light shading members 10 which mask the edges of the image detecting surface 3, thereby limiting the size of the imaging area. By employing the light shading members 10, the point that determines where the angle θ is measured from can be limited to the central area of the plane surface 5, and thus, the image sensor 9 can be positioned closer to the prism 2 than the case shown in FIG. 16. The light shading members 10 may also be used as a guide for positioning the finger tip 1.

Figure 18:
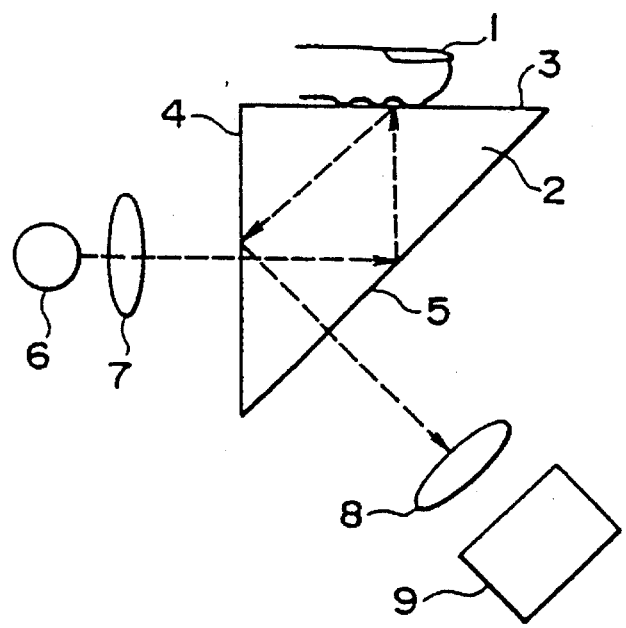
FIG. 18 shows a schematic drawing of a prism, light source and detector according to a sixth embodiment of the present invention.

FIG. 18 shows a sixth embodiment according to the present invention. The sixth embodiment is similar to the fourth embodiment shown in FIG. 16. However, in the sixth embodiment, the lens group 8 and image sensor 9 receive the light reflected by the portion of the finger tip 1 which is in between the lines of the fingerprint, after the light has been reflected by plane surface 4, as shown in FIG. 18.

In the embodiments described above, a triangular a prism 2 is used. However, the prism 2 may be a trapezoidal prism, a pyramidal prism, or a prismoid.

Figure 19:
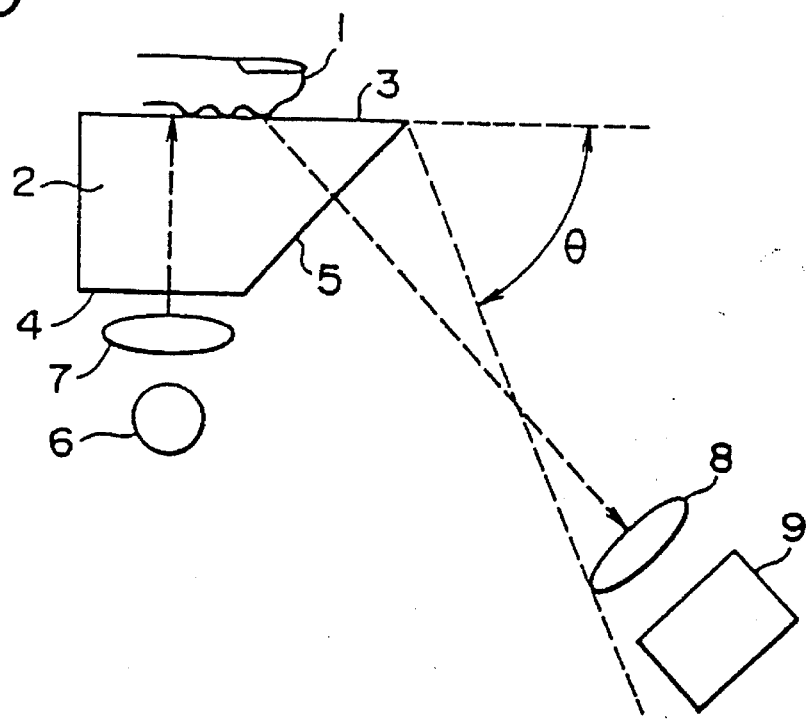
FIG. 19 shows a schematic drawing of a prism, light source and detector according to a seventh embodiment of the present invention.

FIG. 19 shows a seventh embodiment according to the present invention. In the seventh embodiment, the prism 2 has a trapezoidal cross-section. The light source 6 and lens group 7 are located such that the light is incident on the image detecting surface 3 with an incident angle of 0°. The lens group 8 and imaging sensor 9 are located such that the light which emerges at an emerging angle less than θ will be incident on the imaging sensor 9 (similar to the fourth embodiment).

As described above, the present invention provides a fingerprint input apparatus including a light source and image sensor whose positions are specified in relation to a critical angle of incidence of light on an imaging surface. The light source is placed such that the light is always incident on the image detecting surface at an angle less than the critical angle. The image sensor is placed such that it only receives light which emerges at an angle less than θ. As a result, only light which is incident on the image detecting surface where the finger tip is in direct contact (i.e., between the lines of the finger print) will be reflected such that it emerges at an angle less than θ. Thus, with the above-mentioned configuration, a high contrast image of a pattern of the fingerprint can be obtained.

The present disclosure relates to subject matter contained in Japanese Patent Application No. HEI 5-148,774 filed on Jun. 21, 1993, which is expressly incorporated herein by reference in its entirety.

What is claimed is:

1. A fingerprint input apparatus used to detect an image of a fingerprint, comprising:

an optical transparent block having an index of refraction which is greater than an index of refraction of a medium surrounding said optical transparent block, said optical transparent block having an image detecting surface, wherein the finger is placed on at least a portion of said image detecting surface:

light emitting means for emitting light towards said image detecting surface, said light emitting means being positioned such that light emitted by said emitting means is incident on said image detecting surface at an angle less than a critical angle from within said optical transparent blocks; and image sensing means for receiving only light diffused at said image detecting surface and directed to said image sensing means without internal reflection in said optical transparent block, wherein said image sensing means are positioned so that said light diffused at said image detecting surface only reaches said image sensing means when diffused at an angle greater than said critical angle and when undeflected internally within said optical transparent block;

said optical transparent block further comprising at least two other surfaces, said image sensing means facing one of said at least two other surfaces;

an additional light emitting means, said optical transparent block comprising a triangular prism, said light emitting means being positioned such that light is incident on said one of said at least two other surfaces, and is then incident on said image detecting surface, and said additional light emitting means being positioned such that light is incident on said other of said at least two surfaces, and is then incident on said image detecting surface.

2. The fingerprint input apparatus according to claim 1, said image detecting surface comprising light shading means for limiting an area of said image detecting surface illuminated by said light emitting means.

3. The fingerprint input apparatus according to claim 1, said surrounding medium being air.

4. The fingerprint input apparatus according to claim 1, said image detecting surface comprising a plane surface.

5. The fingerprint input apparatus according to claim 1, wherein said light emitting means and said image sensing means are positioned with respect to said optical transparent block such that light emitted from said light emitting means and specularly reflected from said image detecting surface is prevented from being incident upon said image sensing means.

6. The fingerprint input apparatus according to claim 1, wherein said image sensing means are positioned within an area defined by an angle θ measured with respect to said image detecting surface, the angle θ being defined by the following equation:

$$\theta = (\pi/2) - \alpha + \sin^{-1}\{n \sin(\alpha - \gamma)\}$$

where α defines an apical angle formed by joining a surface of said optical transparent block through which light directed to said image sensing means passes, with said image detecting surface;

n equals said index of refraction of said optical transparent block; and

γ equals and angle of incidence of the light on said image detecting surface.

7. A fingerprint input apparatus used to detect an image of a fingerprint, comprising:

an optical transparent block having an index of refraction which is greater than an index of refraction of a medium surrounding said optical transparent block, said optical transparent block having an image detecting surface, wherein the finger is placed on at least a portion of said image detecting surface;

light emitting means for emitting light towards said image detecting surface, said light emitting means being positioned such that light emitted by said emitting means is incident on said image detecting surface at an angle less than a critical angle from within said optical transparent block; and image sensing means for receiving only light diffused at said image detecting surface and directed to said image sensing means without internal reflection in said optical transparent block, wherein said image sensing means are positioned so that said light diffused at said image detecting surface only reaches said image sensing means when diffused at an angle greater than said critical angle and when undeflected internally within said optical transparent block;

said optical transparent block further comprising at least two other surfaces, said image sensing means facing one of said at least two other surfaces;

an additional light emitting means, said light emitting means being positioned such that light is incident on said one of said at least two other surfaces and is then incident on said image detecting surface, and said additional light emitting means being positioned such that light is incident on said other of said at least two other surfaces and is then incident on said image detecting surface.

8. The fingerprint input apparatus according to claim 7, said image detecting surface comprising light shading means for limiting an area of said image detecting surface illuminated by said light emitting means.

9. A fingerprint input apparatus used to detect an image of a fingerprint, comprising:

an optical transparent block having an index of refraction which is greater than an index of refraction of a medium surrounding said optical transparent block, said optical transparent block having an image detecting surface, wherein the finger is placed on at least a portion of said image detecting surface;

light emitting means for emitting light towards said image detecting surface, said light emitting means being positioned such that light emitted by said emitting means is incident on said image detecting surface at an angle less than a critical angle from within said optical transparent block; and image sensing means for receiving only light diffused at said image detecting surface and directed to said image sensing means without internal reflection in said optical transparent block, wherein said image sensing means are positioned so that said light diffused at said image detecting surface only reaches said image sensing means when diffused at an angle greater than said critical angle and when undeflected internally within said optical transparent block;

said optical transparent block further comprising at least two other surfaces, said image sensing means facing one of said at least two other surfaces;

said light emitting means facing said other of said at least two other surfaces, said other of said at least two other surfaces being inclined with respect to said image detecting surface.

10. The fingerprint input apparatus according to claim 9, said image detecting surface comprising light shading means for limiting an area of said image detecting surface illuminated by said light emitting means.

11. The fingerprint input apparatus according to claim 9, said optical transparent block comprising a triangular prism.

12. A fingerprint input apparatus used to detect an image of a fingerprint, comprising:

an optical transparent block having an index of refraction which is greater than an index of refraction of a medium surrounding said optical transparent block, said optical transparent block having an image detecting surface, wherein the finger is placed on at least a portion of said image detecting surface;

light emitting means for emitting light towards said image detecting surface, said light emitting means being positioned such that light emitted by said emitting means is incident on said image detecting surface at an angle less than a critical angle from within said optical transparent block; and image sensing means for receiving only light diffused at said image detecting surface and directed to said image sensing means without internal reflection in said optical transparent block, wherein said damage sensing means are positioned so that said light diffused at said image detecting surface only reaches said image sensing means when diffused at an angle greater than said critical angle and when undeflected internally within said optical transparent block;

said optical transparent block further comprising at least two other surfaces, said image sensing means facing one of said at least two other surfaces said light emitting means facing the other of said at least two other surfaces, said light emitting means positioned so that light emitted from said light emitting means is incident on said other of said at least two other surfaces of said optical transparent block, said other of said at least two other surfaces extending perpendicular to said image detecting surface.

13. The fingerprint input apparatus according to claim 12, said image detecting surface comprising light shading means for limiting an area of said image detecting surface illuminated by said light emitting means.

14. The fingerprint input apparatus according to claim 12, said optical transparent block comprising a triangular prism.

15. The fingerprint input apparatus according to claim 12, said optical transparent block comprising a right-angled prism, said image detecting surface and said other of said at least two other surfaces forming a right angle, and said light emitting means being positioned such that light emitted by said light emitting means is incident on said other of said at least two other surfaces, and is internally reflected by said one of said at least two other surfaces, to be incident on said image detecting surface, at a right angle to said image detecting surface.

* * * * *

UNITED STATES PATENT AND TRADEMARK OFFICE
CERTIFICATE OF CORRECTION

PATENT NO. : 5,623,553
DATED : April 22, 1997
INVENTOR(S) : Takaomi SEKIYA

It is certified that error appears in the above-indentified patent and that said Letters Patent is hereby corrected as shown below:

At column 7, line 63 (claim 1, line 14), change "blocks;" to ---block;---.

At column 8, line 16 (claim 1, line 33), before "surfaces," insert ---other--- .

Signed and Sealed this

Second Day of September, 1997

Attest:

BRUCE LEHMAN

Attesting Officer

Commissioner of Patents and Trademarks